United States Patent [19]
Grandjean

[11] Patent Number: 5,296,229
[45] Date of Patent: Mar. 22, 1994

[54] FLEXIBLE, ELASTIC AND BIODEGRADABLE FILM MADE OF POLYMER BASED ON LACTIC ACID, CAPABLE OF BEING SUITABLE ESPECIALLY FOR THE PRODUCTION OF MEDICAL DRESSINGS

[75] Inventor: Dominique Grandjean, Brussels, Belgium

[73] Assignee: Solvay (Societe Anonyme), Brussels, Belgium

[21] Appl. No.: 915,543

[22] Filed: Jul. 20, 1992

[30] Foreign Application Priority Data

Jul. 19, 1991 [DE] Fed. Rep. of Germany ..... 09100686

[51] Int. Cl.$^5$ ............................................. A61L 15/64
[52] U.S. Cl. ..................................... 424/444; 424/445
[58] Field of Search .................... 424/422, 423, 78.06, 424/444, 445, 486, 488; 524/773

[56] References Cited

U.S. PATENT DOCUMENTS

| | | |
|---|---|---|
| 3,636,956 | 1/1972 | Schneider ............................ 528/354 |
| 3,867,190 | 2/1975 | Schmitt et al. . |
| 4,306,552 | 12/1981 | Gregory . |
| 5,110,852 | 5/1992 | Gogolewski et al. ............... 524/108 |

*Primary Examiner*—Thurman K. Page
*Assistant Examiner*—Peter F. Kulkosky
*Attorney, Agent, or Firm*—Spencer, Frank & Schneider

[57] ABSTRACT

The film is obtained directly by extrusion from the lactic acid-based polymer plasticised beforehand by incorporation of 5 to 30% by weight of the polymer of a glycerol ester obtained from an acid containing 4 carbon atoms in its molecule.

The film has an elongation at break of more than 300% and is particularly suitable for the production of medical dressings.

7 Claims, No Drawings

FLEXIBLE, ELASTIC AND BIODEGRADABLE FILM MADE OF POLYMER BASED ON LACTIC ACID, CAPABLE OF BEING SUITABLE ESPECIALLY FOR THE PRODUCTION OF MEDICAL DRESSINGS

The present invention relates to a flexible elastic and biodegradable film made of polymer based on lactic acid, capable of being suitable especially for the production of medical dressings.

Patent BE-A-778,126 describes the production of absorbable surgical articles and especially of medical dressings from lactic acid polymers.

According to this document lactic acid polymers can actually be spun and the filaments thus produced can be twisted, interwoven, braided or can be arranged in parallel to obtain fabrics capable of being used especially for the production of medical dressings.

The production of dressings according to this document consequently involves at least the successive operations of spinning, weaving and packaging.

The Applicant Company has consequently envisaged to simplify this process by attempting to produce directly, by extrusion, a thin film of these polymers, which can be suitable especially for the production of dressings, but it has found that such a film is difficult to extrude and that, furthermore, the film thus produced has an elasticity and especially an elongation break which are too low to allow its use to be envisaged in the form of medical dressings.

To overcome these problems, the Applicant Company has therefore envisaged incorporating various plasticisers in these polymers to facilitate extrusion and to try and improve the properties of the films obtained, but it has thus found that the usual plasticisers do not produce any satisfactory results.

Tests undertaken with other plasticisers, especially of the glycerol ester type, were also found to be negative. Thus, it appeared, in particular, that glycerol trioleate and glycerol tridecanoate are not compatible with polymers derived from lactic acid, that propylene glycol, glycerol trihexanoate and glycerol result in products which have a resistance to elongation which is too low, that glycerol triacetate or triacetin gives products exhibiting a defective heat resistance and that, finally, other products such as lactates or citrates do not produce any plasticising effect.

After numerous disappointing trials the Applicant Company has finally been able to detect a special type of plasticiser which gives full satisfaction both with regard to the extrusion and with regard to the mechanical properties of the films obtained.

The present invention consequently relates to a flexible, elastic and biodegradable film made of polymer based on lactic acid capable of being suitable especially for the production of medical dressings, which is characterised in that it is produced by extrusion of the lactic acid-based polymer, plasticised beforehand by incorporation of 5 to 30% by weight of the polymer of a glycerol ester obtained from an acid containing 4 carbon atoms in its molecule.

It has been found, in fact, that this type of plasticiser permits the direct production, by extrusion, of flexible films with satisfactory elastic behaviour and exhibiting an elongation at break which is greater than 300%.

The lactic acid-based polymers which can be employed for producing the film according to the invention are chosen from thermoplastic polymers resulting from the homopolymerisation of L-lactic acid, and from the copolymerisation of L-lactic acid and D-lactic acid in a proportion of 99 to 55% of L-lactic acid and/or with other copolymerisable monomers. These other copolymerisable monomers may be, for example, glycolic acid, beta-propiolactide,tetramethylglycolide,-beta-butyrolactone, gamma-butyrolactone, pivalolactone, alpha-hydroxy-acetic acid, alpha-hydroxybutyric acid, alpha-hydroxyisobutyric acid, alpha-hydroxyvaleric acid, alpha-hydroxyisovaleric acid, alpha-hydroxycaproic acid, alphahydroxyisocaproic acid, alpha-hydroxy-alpha-ethylbutyric acid, alpha-hydroxyheptanoic acid, alpha-hydroxystearic acid and the like.

The copolymers which can be employed may be both random copolymers and block copolymers.

The preferred polymers for production of the film according to the invention are the copolymers of DL-lactic acid and of glycolic acid, containing from 25 to 75%, and preferably approximately 50%, by weight of units derived from lactic acid. The use of a copolymer containing, at the same time, units derived from L-lactic acid and D-lactic acid has the advantage of permitting an adjustment of the biodegradation period of the film produced, by modifying the content of units derived from D-lactic acid in the copolymer, it being possible for this content generally to vary between 1 and 50%.

As a general rule, it is preferred to use polymers based on lactic acid which have an inherent viscosity of between 0.5 and 1.

The use of a plasticiser consisting of a glycerol ester derived from an acid containing 4 carbon atoms and, more particularly, of a triester such as glycerol tributanoate or tributyrin is critical for obtaining directly by extrusion a flexible film exhibiting an elongation at break and a satisfactory elastic behaviour, in particular, for the use of this film in the form of medical dressings. The use of other glycerol esters derived from acids containing 4 carbon atoms in their molecule, such as especially glycerol triisobutanoate is, however, not excluded from the scope of the present invention.

The polymer used may advantageously contain from 5 to 30% by weight of plasticiser in relation to the weight of polymer, a content of between 20 and 25% by weight being, however, preferred.

The extruded film may have a thickness which may vary between 25 and 1000 microns and more, a thickness of between 25 and 100 microns being preferred when the film is intended to be used for the production of medical dressings.

The film, in accordance with the invention, has a relatively low water permeability. However, it has been found that it is possible, if desired, to produce a film exhibiting a higher water permeability by incorporating in the starting polymer from 1 to 30%, and preferably from 5% to 25% by weight of the polymer of at least one alkylated cellulose. Hexapropyl methyl cellulose (HPMC) and hexapropyl cellulose (HPC), which are preferred, may be especially mentioned by way of a nonlimiting example of alkylated celluloses which can be used to good effect.

It has also been found that the film in accordance with the invention has a good gas permeability, in particular for oxygen and carbon dioxide. Moreover, the oxygen permeability is further improved, particularly in a moist atmosphere, when the film is extruded by starting with compositions containing an alkylated cellulose.

When intended to be used as a medical dressing, the film in accordance with the invention may also contain any pharmaceutical product such as, for example, an antiinfection agent which is released gradually during the biodegradation of the film.

To produce the film according to the invention it suffices, in principle, to mix the various constituents and then to extrude the mixture with the aid of a conventional extrusion equipment which is suitable for film production.

The mixture of the constituents is preferably produced in a mixer, for example of the Hobart type. When the composition to be extruded must contain an alkylated cellulose, it is generally preferred to introduce the lactic acid-based polymer and the plasticiser into the mixer first and, after a first mixing operation, then to incorporate the alkylated cellulose.

The mixture thus obtained can then be granulated on an extruder, preferably of the single-screw type and may be optionally stored. In this latter case, however, it is appropriate that the granules should be stored at a temperature below 20° C. to avoid any risk of setting up.

The film production equipment may be of any type, but care must be taken to prevent the processed product being heated, during its processing, to a temperature which can result in the degradation of the lactic acid-based polymer.

The film in accordance with the invention and the method of its production are, furthermore, described in greater detail in the illustrated examples which follow.

EXAMPLE 1

Into a Hobart mixer are introduced 100 parts by weight of a copolymer of DL-lactic acid and of glycolic acid, containing 50% by weight of units derived from lactic acid and 22 parts by weight of glycerol tributanoate and, after 5 minutes' mixing, 5 parts by weight of hexapropyl methyl cellulose. After a new 5-minute mixing period the product obtained is introduced into a Reifenhauser single-screw extruder fitted with a granulator.

The screw employed in this extruder applies a compression ratio of 2.5 and the temperatures ranging from the feed zone to the extrusion head are 40° C.-55° C.-60° C.-65° C.-70° C.

The granules thus produced are then introduced into a Clextral BC 21 extruder fitted with a Verbruggen type flat die 100 mm in width.

The screws have an L/D ratio of 36 and a length of 900 mm. The internal diameter of the screws is 17 mm and the external diameter is 25 mm.

The profile of the screws employed is the following:
a conveying zone of 225 mm
a mixing zone of 100 mm
a second conveying zone of 575 mm The heating temperatures displayed, ranging from the feed zone to the die are 55° C.-75° C.-80° C. -85° C.-85° C.-85° C.-90° C.-90° C.-90° C.-90° C.-90° C.-100° C.

The speed of rotation of the screws is programmed at 210 rev/min.

The thickness of the film, its elongation at break and its elasticity modulus are then measured on test pieces of the film thus produced.

The elongation at break is measured by traction in normal environment (23° C. and 50% humidity) on test pieces 200 mm in length and 25 mm in width, the speed of traction being 200 mm/min.

The elasticity modulus expressed in MPa, is determined by the initial elongation force.

The results obtained are the following:
thickness : 0.256 mm.
elongation: 457%.
modulus: 47 MPa.

EXAMPLE 2

The procedure is as in Example 1, but with hexapropyl methyl cellulose replaced with an identical proportion of hexapropyl cellulose.

The results obtained are the following:
thickness : 0.311 mm.
elongation: 515%.
modulus: 71 MPa.

EXAMPLE 3R

By way of a comparative example, a film was produced by pressing, starting with the copolymer of Example 1, free from any additives.

The results obtained are the following:
thickness 0.110 mm.
elongation: 2%.
modulus: 3562 MPa.

It appears that this film exhibits an elongation at break and an elasticity modulus which are totally unsuitable for its use in the form of a medical dressing.

EXAMPLES 4 TO 12

The procedure of Example 1 was employed to produce a series of films, starting from compositions listed in Table 1 below and their thickness and their water permeability were measured.

The results obtained are listed in Table 1.

TABLE 1

| Formulation | Permeability (g/m² · 24 h) | Thickness mm |
| --- | --- | --- |
| PLG* + 15 phr TRIB* | 86 | 0.110 |
| PLG + 15 phr TRIB + 10 HPMC* | >9000 | 0.120 |
| PLG + 15 phr TRIB + 15 HPMC | >9000 | 0.100 |
| PLG + 20 phr TRIB | 105 | 0.100 |
| PLG + 20 phr TRIB + 10 HPMC | >9000 | 0.120 |
| PLG + 20 phr TRIB + 15 HPMC | >9000 | 0.100 |
| PLG + 25 phr TRIB | 129 | 0.090 |
| PLG + 25 phr TRIB + 10 HPMC | >9000 | 0.090 |
| PLG + 25 phr TRIB + 15 HPMC | >9000 | 0.100 |

*PLG = Copolymer of Example 1
TRIB = glycerol tributanoate
HPMC = hexapropyl methyl cellulose

I claim:

1. A flexible, elastic and biodegradable film, wherein said film has less bubbles, less self-sticking and improved thermal stability, produced by extrusion of a copolymer of DL-lactic acid and glycolic acid, containing from 25 to 75 by weight of units derived from lactic acid, and said copolymer plasticised beforehand by incorporation of 5 to 30% by weight of the copolymer of a glycerol ester obtained from an acid containing 4 carbon atoms in its molecule.

2. Film according to claim 1, characterised in that it has an elongation at break of at least 300%.

3. Film according to claim 1, characterised in that the plasticiser is glycerol tributanoate.

4. Film according to claim 1, characterised in that the extruded DL-lactic acid and glycolic acid copolymer additionally contains from 1 to 30% by weight of the polymer of an alkylated cellulose.

5. Film according to claim 4, characterised in that the alkylated cellulose is chosen from the group consisting of hexapropyl cellulose and hexapropyl methyl cellulose.

6. Film according to claim 1, characterised in that is additionally contains a pharmaceutical product.

7. Medical dressing produced from a film obtained according to claim 1.

* * * * *